United States Patent
Delache et al.

(10) Patent No.: US 7,500,481 B2
(45) Date of Patent: Mar. 10, 2009

(54) APPARATUS TO ASSIST A PATIENT'S BREATHING WITH A VARIABLE RAMP PERIOD TO RISE TO TREATMENT PRESSURE

(75) Inventors: Alain Delache, Nice (FR); Véronique Delache, Nice (FR)

(73) Assignee: Kaerys S.A., Nice (FR)

( * ) Notice: Subject to any disclaimer, the term of this patent is extended or adjusted under 35 U.S.C. 154(b) by 806 days.

(21) Appl. No.: 10/506,979

(22) PCT Filed: Mar. 10, 2003

(86) PCT No.: PCT/IB03/01422

§ 371 (c)(1),
(2), (4) Date: Sep. 8, 2004

(87) PCT Pub. No.: WO03/075991

PCT Pub. Date: Sep. 18, 2003

(65) Prior Publication Data

US 2005/0166920 A1    Aug. 4, 2005

Related U.S. Application Data

(60) Provisional application No. 60/362,441, filed on Mar. 8, 2002.

(51) Int. Cl.
*A61M 16/00* (2006.01)
*A62B 7/00* (2006.01)
*F16K 31/02* (2006.01)

(52) U.S. Cl. ............ 128/204.23; 128/205.23; 128/204.26; 128/204.21; 128/204.18; 128/203.14; 128/203.13; 128/203.12; 128/204.29; 128/205.11; 128/205.18

(58) Field of Classification Search ............ 128/204.23, 128/205.23, 204.26, 204.21, 204.18, 203.14, 128/203.13, 203.12, 204.29, 205.11, 205.18
See application file for complete search history.

(56) References Cited

U.S. PATENT DOCUMENTS

| 5,245,995 | A | 9/1993 | Sullivan et al. | ........ 128/204.23 |
| 5,503,146 | A | 4/1996 | Froehlich et al. | ....... 128/204.23 |

(Continued)

FOREIGN PATENT DOCUMENTS

EP    0 821 976    2/1998

(Continued)

*Primary Examiner*—Patricia M Bianco
*Assistant Examiner*—Nihir Patel
(74) *Attorney, Agent, or Firm*—Westerman, Hattori, Daniels & Adrian, LLP.

(57) ABSTRACT

An apparatus (1) to assist a patient's respiration by delivering air to a patient through a mask (20), including a ramp module (10) connected to a control unit (2) to provide the control unit with a pressure value $P_M$ at mask (20), so that when apparatus (1) starts functioning, the pressure progressively rises until it reaches a treatment pressure PTi, the apparatus further including a comparator connected to ramp module (10), at least one device for detecting the patient's breathing parameters and sending them to the comparator, so that the comparator can determine whether an event ($E_1$, $E_2$ or $E_3$) occurs in patient's breathing and to send the corresponding data to ramp module (10) which provides control unit (2) with a pressure value $P_M$ that will speed up with respect of time, so that the pressure rise at patient's mask (20) is accelerated.

9 Claims, 2 Drawing Sheets

U.S. PATENT DOCUMENTS

| | | | |
|---|---|---|---|
| 5,970,975 A * | 10/1999 | Estes et al. | 128/204.23 |
| 5,977,737 A | 11/1999 | Labriola, II | 318/599 |
| 2002/0000228 A1 | 1/2002 | Schoeb | 128/204.19 |
| 2002/0014239 A1 | 2/2002 | Chalvignac | 128/18 |
| 2004/0187870 A1* | 9/2004 | Matthews et al. | 128/204.22 |

FOREIGN PATENT DOCUMENTS

| | | |
|---|---|---|
| EP | 1 166 813 | 1/2002 |
| EP | 1 177 810 | 2/2002 |
| WO | WO 92/11054 | 7/1992 |
| WO | WO 98/57691 | 12/1998 |
| WO | WO 02/26305 | 4/2002 |
| WO | WO 02/053217 | 7/2002 |

* cited by examiner

APPARATUS TO ASSIST A PATIENT'S BREATHING WITH A VARIABLE RAMP PERIOD TO RISE TO TREATMENT PRESSURE

This application is a U.S. National Stage of International Application PCT/IB03/01422, filed Mar. 10, 2003, and claims priority of U.S. provisional application Ser. No. 60/362,441, filed Mar. 8, 2002.

TECHNICAL FIELD

This invention concerns the field of apparatus to assist a patient respiration and more specifically an apparatus bringing progressively to the pressure of treatment the air the patient is provided with.

BACKGROUND ART

In many treatments apparatus are used to provide patients with air. More frequently they are used for patients with a breathing deficiency caused for example by the weakness of the breathing system or by obstructive apneas during the sleep. In those cases it is important to control the pressure of the air delivered to the patient. With respiratory insufficient patients, apparatus providing air at a higher pressure help to compensate the weakness of the patients lungs. In the case of patients suffering of sleep apneas, providing the air at a higher pressure removes the obstruction of the upper airways.

The pressure of treatment is usually not strong enough to wake the patient up, but can prevent him from falling asleep. An implementation of treatments apparatus is to wait for the patient to fall asleep before providing air under the treatment pressure. The classical solution is to have a ramp period, which is a slow increase of the delivered pressure from a low level to the treatment pressure.

Still to enhance the comfort of the patient, it is disclosed in patent U.S. Pat. Nos. 5,492,113 and 5,970,975 an apparatus wherein several cycles of ramp are provided on patient's conscious demand. The cycles actuated after the first cycle rise faster in pressure. All those ramps are predetermined in shape and duration. The patient can also select a fastest shape of ramp or select one special shape in order to fall asleep more easily. This selection being made among different predetermined shapes of ramp. However, such devices require from the patient a minimum of consciousness to activate the ramp cycles. This is not really very efficient to fall asleep and it is not possible when the patient has fallen asleep.

Moreover each ramp can not be modified during the time when the ramp is activated.

SUMMARY OF THE INVENTION

The first object of the invention is to provide a ramp that would be able to modulate automatically, especially when the patient falls asleep.

A second object of the invention is to provide in any case a maximum of time in rise of pressure, in order to apply the treatment in any case.

The invention thus concerns an apparatus to assist a patient's respiration by delivering air to a patient through a mask, comprising:

a blower to provide the patient with air under a treatment pressure, a control unit to adjust the pressure delivered by the blower at the level of the patient's mask, a ramp module connected to the control unit in order to provide the control unit with the value of pressure $P_M$ to settle at the mask, so that when the apparatus starts functioning, the pressure progressively rises until the pressure of treatment $P_T$;

the apparatus comprising a comparator connected to the ramp module, means for detecting the patient's breathing parameters and sending them to said comparator, in order that in response to breathing parameters, the comparator is able to determine that an event occurs in patient's breathing and to send the corresponding data to the ramp module which provides the control unit with a value of pressure $P_M$ that will speed up with respect of the time, so that the rise of pressure at patient's mask is accelerated.

In an implementation of the invention, the value of pressure $P_M$ has always maximum and/or minimum limits so that the increase of pressure is also limited in minimum and/or maximum.

Such an apparatus has the advantage to generate a ramp period which can be modulated in the same ramp, according to patient's breathing parameters.

BRIEF DESCRIPTION OF FIGURES

The purposes, objects and characteristics of the invention will become more apparent from the following description when taken in conjunction with the accompanying drawings in which.

DETAILED DESCRIPTION OF THE INVENTION

The apparatus according to the present invention is able to generate a ramp period which can be modulated in respect of the time required by the patient for falling asleep.

Figure 1:
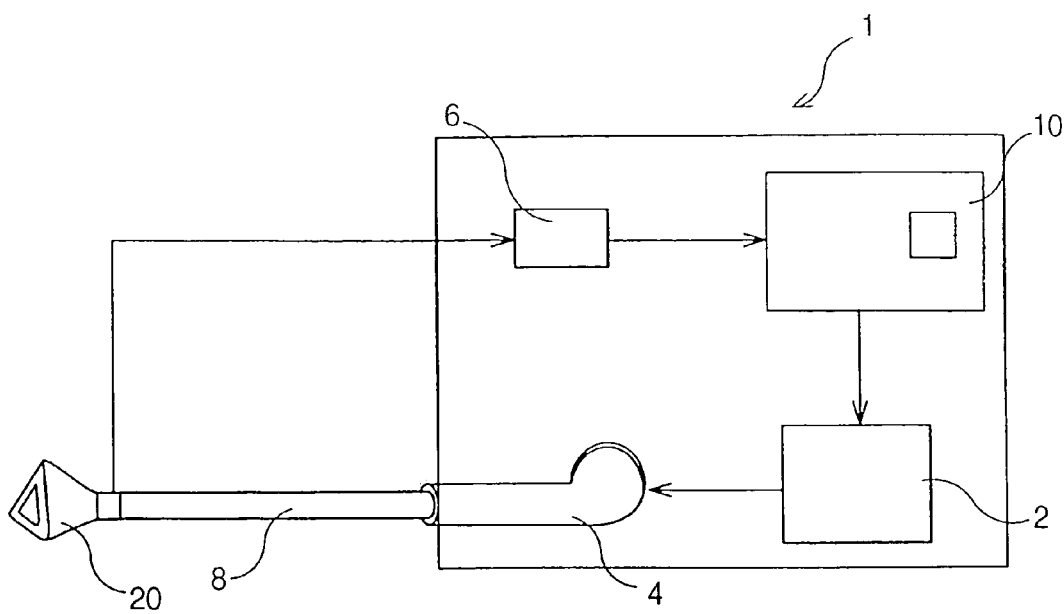
FIG. 1 represents the apparatus schema.

The apparatus as represented in FIG. 1 comprises a blower 4 to provide the patient with air. This blower is connected to a tube 8 on a first extremity, the second extremity being connected to the mask 20 wherein the patient breathes. A control unit 2 provides the blower 4 with the electrical control required to enable the blower to function in order to set a given pressure at the patient's mask or blower's outlet. This pressure could be measured by a pressure transducer 6 at the mask level or at the tube extremity, which is connected to the mask. A ramp module 10 is connected to the control unit 2 and to the pressure transducer 6. The ramp module provides the control unit 2 with the pressure at the patient's mask and with the pressure to settle at the patient's mask at the starting of the apparatus 1 functioning. During the treatment the control unit 2 is able to detect breathing events according to the pressure sensor 6 or any other way to evaluate or measure the patient's airflow. Such detection can be given by airflow sensors which provide the control unit with ressure parameters, the control units being thus able to detect that an event is occurring.

The apparatus according to the present invention is able to modulate the rise in pressure during one single ramp period, which is impossible to perform for apparatus of prior art. The apparatus comprises a ramp module 10 connected to the control unit 2 in order to provide the control unit with the value of pressure $P_M$ to settle at the patient's mask, so that when said apparatus starts functioning, the pressure progressively rises until the pressure of treatment $P_T$. The apparatus comprises a comparator which is not represented in FIG. 1 and that can be comprised in the control unit 2. This comparator is connected to the ramp module 10. The apparatus comprise also at least one means for detecting the patients breathing parameters and sending them to said comparator, in order that in response to said breathing parameters, the comparator is able to determine that an event occurs in patient breathing and to send the corresponding data to the ramp module which provide the control unit 2 with a value of pressure $P_M$ that will speed up in respect of the time, so that the rise of pressure at patient's mask is accelerated.

According to a preferred embodiment, the ramp module 10 provides the value of pressure $P_M$ being a linear function of time wherein the increase coefficient $K_{RP}$ is constant, said ramp module increasing that coefficient of a constant value $K_E$ when the control unit 2 send a data corresponding to the event which occurred.

Figure 3:
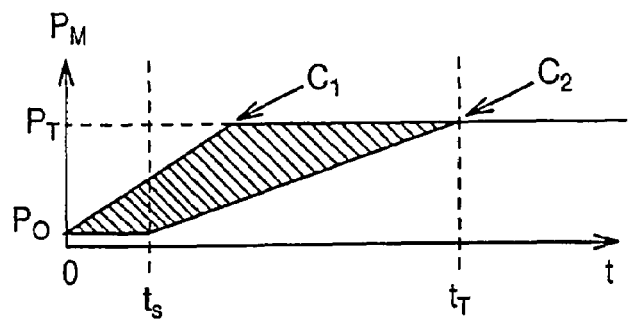
FIG. 3 represents the domain of pressure increase.

In the apparatus 1 according to the present invention, a minimum speed of rise in pressure until the treatment pressure is set, as represented by the curve $C_2$ on FIG. 3. This minimum rise of pressure in respect of time is called in the present application a safety ramp $C_2$. Before the ramps period starts at the instant $t_S$, a minimum starting pressure $P_0$ is delivered. After the instant $t_S$, even if the patient is not asleep, the pressure at the mask will start rising. In any case at the instant $t_T$, the treatment pressure will be reached; this means that the curve C2 represents the minimum speed of rise in pressure. In a preferential implementation of the invention, the minimum speed of rise in pressure is proportional to time, the coefficient to rise in pressure according to time being $K_{SR}$. Also it can be set a maximum of rise in pressure as represented by the curve $C_1$ on FIG. 3. The maximum of rise in pressure can also be given a linear function of time. Between these two limits the rising of the pressure can be modulated by the control unit 2 in respect of the patient's falling asleep. That is to say that whenever any events occurs or not, the pressure provided at the patient's mask $P_{PM}$ before the time of plain treatment $t_T$ will be comprised between these two limits, this domain of pressure variations being represented in FIG. 3 by the hachures.

Figure 4:
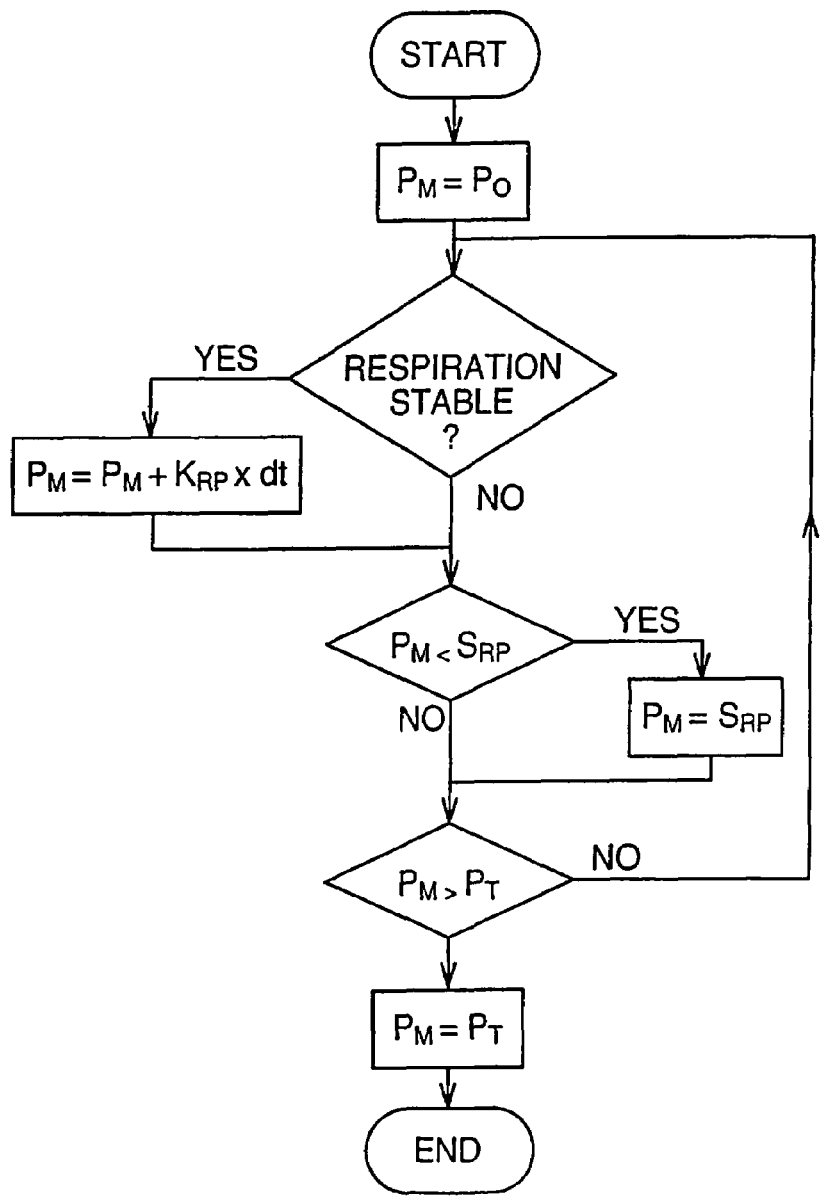
FIG. 4 represents the block diagram for the ramp period.

When a patient is asleep his respiration becomes stable, this is used to detect the instant when the patient falls asleep. Another way to detect when the patient falls asleep is to detect the drop of frequency between the awake rate breathing and the awake breathing. As represented in FIG. 4 and according to a preferential implementation, the control unit 2 transmits to the ramp module an output average pressure value $P_M$ which is the pressure value required to be delivered to the patient's mask. When the patient is about to fall asleep, his respiration becomes stable. In that case the $P_M$ value is increased, preferentially as a linear function of time, the proportional coefficient being $K_{RP}$. If the pressure value $P_M$ is inferior to the safety ramp pressure $S_{RP}$, the pressure $P_M$ is set to the value of the safety ramp pressure $S_{RP}$, which is in a preferential implementation calculated by the ramp module 10 by multiplying the time spent from the beginning of the ramp routine to the present time by the coefficient $K_{SP}$. When the pressure value $P_M$ equals or is superior to the treatment pressure $P_T$, the $P_M$ pressure is maintained equal to the treatment pressure value $P_T$. On the contrary the control unit 2 checks again if the respiration is stable. This shows that until the patient falls asleep the $P_M$ value will not be superior to the treatment pressure $P_T$, and will only equal it when the patient falls asleep or when the safety ramp reaches the treatment pressure value. This also shows that during the ramp period, if the respiration is stable, the air provided can rise faster than the safety ramp. In that case, the coefficient $K_{RP}$ will be higher than the coefficient $K_{SP}$. The ramp module will thus enable to the control unit to accelerate the rise in pressure when the patients fall asleep and when no events are detected.

Another implementation of the apparatus according to the present invention is that when the control unit detects an event in patients breathing that shows an asleep state, the control unit will provide the ramp module 10 with the information. The ramp module will thus increase again the rise in pressure.

The following are examples of ramp periods generated by the apparatus according the present invention.

EXAMPLE 1

Variations of Value $P_M$ According to Different Events

Figure 2:
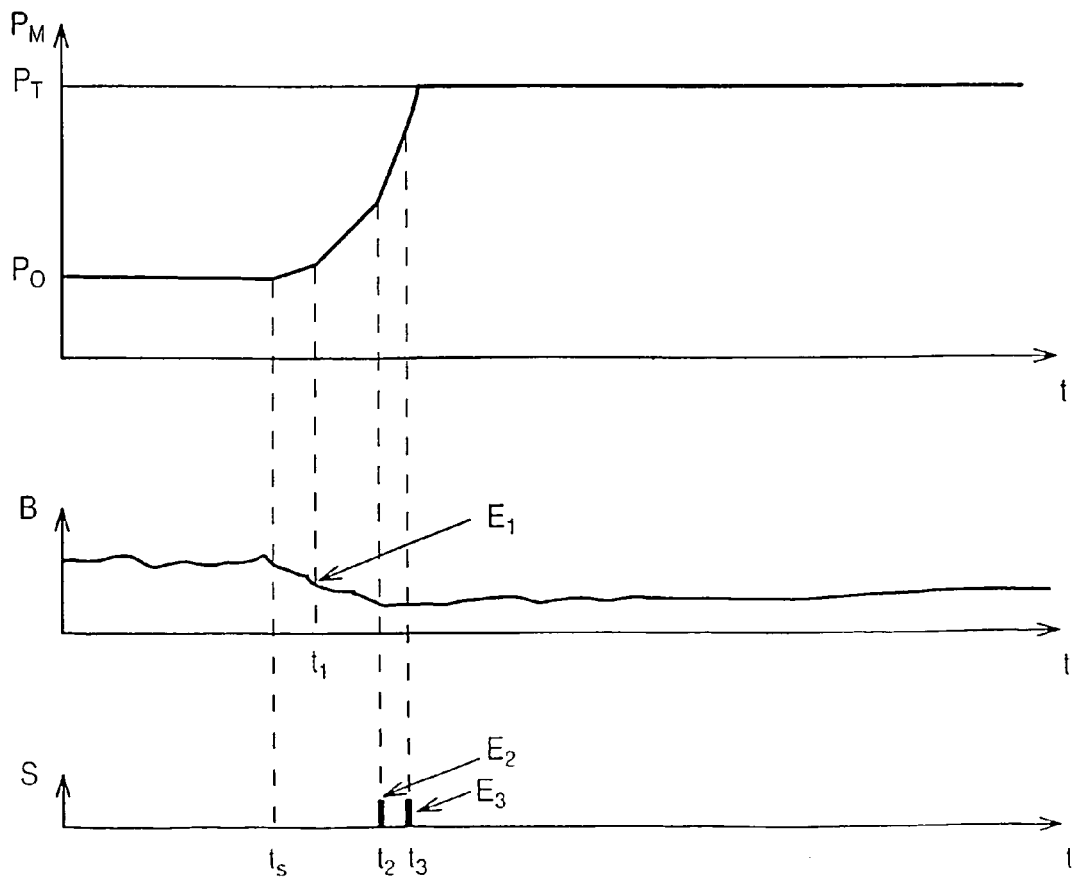
FIG. 2 represents the pressure delivered to the patient's mask according to special events occurring in patient's breathing.

FIG. 2 represents one example of the apparatus functioning wherein three systems of coordinates are represented: pressure value PM as a function of time, patient's breathing B as a function of time and snoring S as a function of time. At a time $t_S$, the ramp module 10 activates the rise in pressure. At time $t_1$ as a slowdown $E_1$ in breathing is detected, the rise in pressure is accelerated by the ramp module 10. Then at time $t_2$ snoring $E_2$ is detected. Thus, the rise in pressure is accelerated again by the ramp module. As at time $t_3$ a snoring $E_3$ is still detected the ramp module still accelerates the rise in pressure. As represented on FIG. 2, the preferred embodiment is a linear rise in pressure. Thus at time $t_S$, the coefficient $K_{RP}$ of rise in pressure is constant. Each time an event is detected the module ramp adds a given constant value $K_E$ to this coefficient, the slope of the linear function being thus accentuated at each event. This will last until the treatment pressure $P_T$ is raised. Then the ramp is completed and the control unit applies the treatment pressure to the patient's mask. The value $K_E$ can be set by the physician in a non volatile memory and can be different according to the event detected.

EXAMPLE 2

Example of Calculating the Value $P_M$

In this example the treatment pressure $P_T$ is of 10 hecto pascal (hPa). The initial pressure $P_0$ of the air provided at patient's mask is 4 hPa. A physician has set that the ramp will start at a time ts of 2 minutes and has set the initial coefficient $K_{RP}$ at 0.2 hPa per minute (hPa/mn). The physician also set that when a snoring is detected $K_E$ equals 1 hPa when the breath rate is below a set threshold.

When the apparatus starts the control units supply the blower in order to set at the patient's mask a pressure of 4 hPa. After 2 minutes, the ramp module starts increasing the value $P_M$. As no events occurs, the coefficient $K_{RP}$ stays at 0.2 hPa. After 10 minutes the value $P_M$ is of 5.6 hPa (8 minutes multiplied by 0.2 hPa/mn and added to the 4 hPa). After these ten minutes, the patient's breath is below threshold. The ramp module adds the corresponding $K_E$ value to the coefficient $K_{RP}$, which thus equals 1.2 hPa/mn. The treatment pressure is thus raised in about 13 minutes and 40 seconds.

The invention claimed is:

1. An apparatus to assist a patient's respiration by delivering air to a patient through a mask, comprising:
   a blower to provide the patient with air under a treatment pressure;
   a control unit to adjust the pressure delivered by said blower at the level of said mask;

a ramp module connected to the control unit in order to provide the control unit with a value of pressure $P_M$ to settle at said mask so that, when said apparatus starts functioning, the pressure progressively rises until the pressure of treatment $P_T$, the rise of pressure until the pressure of treatment $P_T$ corresponding to a ramp period;

a comparator connected to the ramp module; and at least one means for detecting the patient's breathing parameters during said ramp period and sending them to said comparator such that the comparator is able during this said ramp period to determine whether an event ($E_1$, $E_2$ or $E_3$) occurs in patient's breathing based on said breathing parameters and to send the corresponding data to the ramp module which provides the control unit with a value of pressure $P_M$ that will speed up with respect of time during this said ramp period, in order to accelerate the rise of pressure at patient's mask within the same said ramp period.

2. The apparatus according to claim 1, wherein said ramp module provides the value of pressure $P_M$ being a linear function of time wherein an increase coefficient $K_{RP}$ is constant, said ramp module increasing that coefficient of a constant value $K_E$ when the control unit sends a data corresponding to said event ($E_1$, $E_2$ or $E_3$).

3. The apparatus according to claim 1, wherein the value of pressure $P_M$ has always maximum and/or minimum limits so that the increase of pressure is also limited in minimum and/or maximum.

4. The apparatus according to claim 2, wherein said ramp module comprises a memory where a minimum coefficient $K_{SRP}$ is stored, said ramp module always maintaining the coefficient $K_{SRP}$ equal or greater than said minimum coefficient $K_{SRP}$, so that the ramp module provides the control unit with a value of pressure $P_M$ always greater than a minimum limit.

5. The apparatus according to claim 2, wherein said ramp module comprises a memory where a maximum coefficient $K_{MRP}$ is stored, said ramp module always maintaining the coefficient $K_{RP}$ equal or less than said maximum coefficient $K_{MRP}$, so that the ramp module provides the control unit with a value of pressure $P_M$ always less than a maximum limit.

6. The apparatus according to claim 1, wherein said means for detecting the patient's breathing parameters enable the control unit to compute the airflow at patient's mask, said comparator determining whether an event ($E_1$, $E_2$ or $E_3$) is occurring with the airflow parameters or shape.

7. The apparatus according to claim 1, wherein the ramp module increases the value of pressure $P_M$ when an anomaly in patient's breathing is detected.

8. The apparatus of claim 7, wherein said anomaly is either snoring or apnea.

9. The apparatus according to claim 1, wherein the ramp module increases the value of pressure $P_M$ when the patient's breathing parameters correspond to a drop between awake breathing and asleep breathing or when they correspond to a stable frequency of breathing.

\* \* \* \* \*